United States Patent [19]

Jacques et al.

[11] 4,438,042
[45] Mar. 20, 1984

[54] PREPARATION OF AROMATIC/ALIPHATIC NITRILES

[75] Inventors: Roland Jacques, Ales; Michel Reppelin, Collonges-au-Mont-d'Or; Laurent Seigneurin, Salindres, all of France

[73] Assignee: Rhone-Poulenc Specialites Chimiques, Courbevoie, France

[21] Appl. No.: 378,226

[22] Filed: May 14, 1982

[30] Foreign Application Priority Data

May 15, 1982 [FR] France ................. 81 09695

[51] Int. Cl.³ ............................... C07C 120/10
[52] U.S. Cl. .................. 260/465 B; 502/224
[58] Field of Search ............ 260/465 B; 252/441

[56] References Cited

U.S. PATENT DOCUMENTS 4,324,698 4/1982 Lewis et al. ................. 252/455 Z

FOREIGN PATENT DOCUMENTS 1250165 11/1960 France .

*Primary Examiner*—Dolph H. Torrence
*Attorney, Agent, or Firm*—Burns, Doane, Swecker & Mathis

[57] ABSTRACT

Aromatic/aliphatic nitriles having the formula:

$$Ar-A-CN \qquad (I)$$

wherein Ar is phenyl or substituted phenyl and A is a direct chemical bond or a hydrocarbon having from 1 to 6 carbon atoms, are conveniently prepared by heating to a temperature ranging from about 450° C. to about 550° C. a formamide or formanilide having the formula:

$$Ar-A-NHCHO \qquad (II)$$

or an amide having the formula:

$$Ar-A-CONH_2 \qquad (III)$$

in the presence of a fluorinated siliceous catalyst, said catalyst having been prepared by (i) impregnating a particulate silica prepared by the precipitation of sodium silicate with sulfuric acid, with a dilute aqueous solution of hydrofluoric acid, said hydrofluoric acid solution having a concentration in HF of less than about 5% by weight, and the ratio by weight of the hydrofluoric acid contained in said aqueous solution thereof to the silica being less than about 5%, followed by (ii) drying the catalyst thus impregnated.

18 Claims, No Drawings

PREPARATION OF AROMATIC/ALIPHATIC NITRILES

CROSS-REFERENCE TO RELATED APPLICATION

Our copending application, Ser. No. 378,191, filed concurrently herewith and assigned to the assignee hereof.

BACKGROUND OF THE INVENTION

1. Field of the Invention

The present invention relates to the preparation of aromatic or aliphatic nitriles, and, more especially, to the preparation of nitriles having the general formula $$Ar-A-CN \qquad (I)$$

wherein Ar represents a substituted or unsubstituted benzene radical and A represents a direct chemical bond or a hydrocarbon radical having from 1 to 6 carbon atoms, from formamides or formanilides having the general formula:

$$Ar-A-NHCHO \qquad (II)$$

or amides having the general formula $$Ar-A-CONH_2 \qquad (III)$$

wherein Ar and A are as above defined.

2. Description of the Prior Art

It is known to this art, from French Pat. No. 1,250,165, to prepare nitriles from compounds of the aforesaid type (II) by reactively contacting the same, at a temperature ranging from 460° to 560° C., and in the gaseous phase, with a catalyst comprising active silicic acid or silicates containing a metal oxide.

Nonetheless, carrying out the subject reaction with catalysts of the type described in the aforecited French patent evidences that the selectivity realized is not sufficient for optimal industrial utilization of the process. Furthermore, when nitriles of the Formula I are desired, wherein the radical Ar bears a fluorine substituent, the process promotes the formation of heavy by-products which shortens the life of the catalyst by encrusting its surface, and defluorination reactions too are observed, resulting in compounds which are extremely difficult to separate from the desired product.

SUMMARY OF THE INVENTION

Accordingly, a major object of the present invention is the provision of an improved process for the preparation of aromatic or aliphatic nitriles, which improved process is conspicuously devoid of those disadvantages and drawbacks to date characterizing the state of this art.

Another object of the present invention is the provision of an improved process for the preparation of aromatic or aliphatic nitriles from amides having the Formula (III).

Briefly, the present invention features the preparation of aromatic or aliphatic nitriles having the formula:

$$Ar-A-CN \qquad (I)$$

wherein Ar represents a substituted or unsubstituted benzene radical and A represents a direct chemical bond or a hydrocarbon radical having from 1 to 6 carbon atoms, by heating to a temperature ranging from about 450° C. to about 550° C. a formamide or a formanilide having the formula:

$$Ar-A-NHCHO \qquad (II)$$

or an amide having the formula:

$$Ar-A-CONH_2 \qquad (III)$$

wherein Ar and A are as above defined, in the presence of a catalyst prepared by the impregnation with a dilute aqueous solution of hydrofluoric acid having an HF concentration of less than about 5% by weight, of a silica prepared from sodium silicate and sulfuric acid, the ratio by weight of the hydrofluoric acid contained in the aqueous solution to such silica being less than about 5%, followed by the subsequent drying thereof.

DETAILED DESCRIPTION OF THE INVENTION

More particularly according to this invention, by "impregnation of the silica" there is intended the contacting of the silica with an aqueous solution of hydrofluoric acid.

And in a preferred embodiment of the invention, such impregnation is carried out by soaking the silica in the aqueous solution of hydrofluoric acid.

In another preferred embodiment of the invention, such impregnation is carried out by atomizing the aqueous solution of hydrofluoric acid and spraying same upon the silica.

In both of the aforesaid embodiments the amount of hydrofluoric acid introduced into the silica will be approximately equal to the total pore volume of the silica treated.

It has also been determined that, consistent herewith, it is preferable to impregnate a silica having a specific surface ranging from about 200 to about 350 m³/g, a total pore volume ranging from about 50 to about 100 cm³/g, an average pore diameter ranging from about 70 to 100 Å, an exchange pH less than about 7 and a sodium content, expressed in Na$_2$O, of less than about 1% by weight relative to the silica.

In another preferred embodiment of the invention, the impregnation is effected by means of an aqueous solution of hydrofluoric acid having a concentration ranging from about 0.04% to about 4% by weight.

The impregnation is preferably carried out at ambient temperature, under atmospheric pressure.

The ultimate drying is preferably carried out at a temperature ranging from about 150° to about 600° C. for about 1 to 24 hours.

Advantageously, the silica, after drying, contains a total amount of about 0.3% to about 3% by weight of fluorine.

The silica to be impregnated according hereto is obtained in conventional manner, by the precipitation of sodium silicate with sulfuric acid (compare in this respect, for example, French Pat. No. 2,093,196).

By "benzene radical (Ar)" as utilized herein, there is intended a phenyl radical or a phenyl radical containing one or more substituents. Exemplary of such substituents are alkyl and alkoxy radicals having from 1 to 6 carbon atoms, phenyl and phenoxy radicals, and the radicals F, CF$_3$, OCF$_3$, SCF$_3$, OH, Cl, Br or CN.

The process according to the invention is more particularly adapted to the use of compounds having Formula II or III, the phenyl radical of which bears one or more of the fluorine substituents F, CF$_3$, OCF$_3$ or SCF$_3$. In this case, a minor amount of reaction products resulting from defluorination is obtained.

The process is even more suited to the use of compounds having the Formula II and bearing a fluorine substituent. Among the latter, meta-trifluoromethylformanilide:

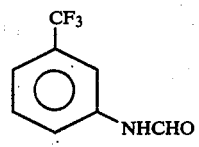

and meta-trifluoromethylbenzylformamide:

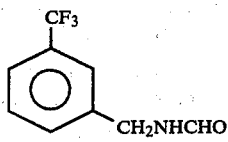

are representative; such compounds give rise to the respective preparation of meta-trifluoromethylbenzonitrile and meta-trifluoromethylphenylacetonitrile which are very important intermediates for the synthesis of a variety of compounds having phytosanitary or pharmaceutical activity. The following compounds are representative of those of Formula II suitable as starting materials in the process of the invention: formanilide, 3-trifluoromethylformanilide, 4-trifluoromethylformanilide, 4-methoxyformanilide, 4-hydroxyformanilide, 2-fluoroformanilide, 3-fluoroformanilide, 4-fluoroformanilide, 2-chloroformanilide, 3-chloroformanilide, 4-chloroformanilide, 2-chloro-5-trifluoromethylformanilide, 3-trifluoromethyl-4-chloroformanilide, 3-phenoxyformanilide, 3,5-bistrifluoromethylformanilide, 2,6-dichloroformanilide, 2,6-difluoroformanilide, 2,4-difluoroformanilide, 3-trifluoromethylthioformanilide, benzylformamide, 3-trifluoromethylbenzylformamide, 4-trifluoromethylbenzylformamide, 4-fluoromethylformamide, 4-chlorobenzylformamide, 2-fluorobenzylformamide, 2-chlorobenzylformamide, 2-trifluoromethoxybenzylformamide, 4-trifluoromethoxybenzylformamide, 2-trifluoromethoxybenzylformamide, 4-trifluoromethoxybenzylformamide, 2-trifluoromethylthiobenzylformamide, 4-trifluoromethylthiobenzylformamide, 2-fluoro-5-methylbenzylformamide, 3-fluoro-6-methylbenzylformamide, 2-chloro-5-trifluoromethoxybenzylformamide, 2-trifluoromethoxy-5-chlorobenzylformamide, 2,5-difluorobenzylformamide, 2,4-difluorobenzylformamide.

And exemplary of the compounds of the Formula III are: 3-trifluoromethylbenzamide, 4-trifluoromethylbenzamide, 2-fluorobenzamide, 3-fluorobenzamide, 4-fluorobenzamide, 3-trifluoromethylphenylacetamide, 4-fluorophenylacetamide, 4-trifluoromethoxyphenylacetamide.

Thus, according to the process of this invention, the following compounds having the Formula I are conveniently prepared: benzonitrile, 3-trifluoromethylbenzonitrile 4-trifluoromethylbenzonitrile, 4-methoxybenzonitrile, 4-hydroxybenzonitrile, 2-fluorobenzonitrile, 3-fluorobenzonitrile, 4-fluorobenzonitrile, 2-chlorobenzonitrile, 3-chlorobenzonitrile, 4-chlorobenzonitrile, 2-chloro-5-trifluoromethylbenzonitrile, 3-trifluoromethyl-4-chlorobenzonitrile, 3-phenoxybenzonitrile, 3,5-bis-trifluoromethylbenzonitrile, 2,6-dichlorobenzonitrile, 2,6-difluorobenzonitrile, 2,4-difluorobenzonitrile, 3-trifluoromethylthiobenzonitrile, 4-trifluoromethoxybenzonitrile, phenylacetonitrile, 3-trifluoromethylphenylacetonitrile, 4-trifluoromethylphenylacetonitrile, 4-fluorophenylacetonitrile, 4-chlorophenylacetonitrile, 2-fluorophenylacetonitrile, 2-chlorophenylacetonitrile, 2-trifluoromethoxyphenylacetonitrile, 4-trifluoromethoxyphenylacetonitrile, 2-trifluoromethylthiophenylacetonitrile, 4-trifluoromethylthiophenylacetonitrile, 2-fluoro-5-methylphenylacetonitrile, 3-fluoro-6-methylphenylacetonitrile, 2-chloro-5-trifluoromethoxyphenylacetonitrile, 2-trifluoromethoxy-5-chlorophenylacetonitrile, 2,5-difluorophenylacetonitrile, 2,4-difluorophenylacetonitrile.

In another, but non-critical embodiment of the invention, the reaction carried out in the presence of a gaseous inert diluent, consisting preferably of nitrogen and/or CO$_2$ and/or acetonitrile.

It is preferred to use acetonitrile in an amount such that the molar percentage of the compound having the Formula II or III in the acetonitrile ranges from about 2 to about 20, and preferably from about 5 to about 10.

The reaction temperature preferably ranges from about 510° to 530° C. when a compound of the Formula II is employed, and from 450° to 480° C. when a compound of the Formula III is employed.

The reaction is typically conducted at atmospheric pressure, albeit pressures greater or less than atmospheric too are within the ambit of the invention.

The process according to the invention is advantageously carried out at a space velocity of from about 0.2 to about 4 moles of the compound II or III per hour and per liter of the catalyst.

The compounds III are per se known to the art and may be prepared by any known method.

Likewise, the preparation of the compounds II, when A is a direct chemical bond, is carried out in a manner well known to this prior art, by the reaction of the corresponding aniline with formic acid.

In the event that A is a hydrocarbon radical such as —CH$_2$—, the compounds II may conveniently be prepared by the reaction, at 0° to 100° C. and in the presence of hydrofluoric acid, of the corresponding benzene derivative ArH with hydroxymethylformamide, HO—CH$_2$—NHCHO. The ratio of ArH to HO—CH$_2$—NHCHO ranges from about 0.5 to about 2, and that of the hydrofluoric acid to the ArH ranges from about 5 to about 50. Such a preparation is featured in Desbois et al copending application, Ser. No. 378,225, filed concurrently herewith and assigned to the assignee hereof.

In order to further illustrate the present invention and the advantages thereof, the following specific examples are given, it being understood that same are intended only as illustrative and in nowise limitative.

EXAMPLE 1

(a) Preparation of the silica (1) A first acid solution containing 1 kg of 98% sulfuric acid and 1 kg of water, and a second aqueous solution of sodium silicate having a density of 1.185 (SiO$_2$/Na$_2$O=3.3), were prepared.

The silicate solution was next poured into the sulfuric acid solution which was under vigorous agitation, while the temperature was maintained from 15° to 20° C. The pouring was discontinued after 1900 g of the sodium silicate solution had been added. The resulting solution gelled in a few minutes. The hydrogel obtained was comminuted into grains and then washed with a flow of water having a pH of from 6 to 7 for 24 hours. The solids obtained were dried at 200° C. for 24 hours.

The characteristics of the final product silica were as follows:

| (i) Specific surface | 420 m²/g |
|---|---|
| (ii) Total pore volume | 75 cm³/100 g |
| (iii) Na₂O content | 900 ppm |
| (iv) Exchange pH | 6.1 |
| (v) Pore diameter | 35 Å |

(2) 2250 g of the above silica were introduced into a reactor containing 3 liters of water. The silica was completely immersed. The mixture was heated until a relative pressure of 0.7 bar was established in the reactor, and which was maintained for 3 hours.

A sample of the silica treated in this manner, had the following characteristics after drying for 24 hours at 200° C.:

| (i) Specific surface | 320 m²/g |
|---|---|
| (ii) Total pore volume | 75 cm³/100 g |
| (iii) Na₂O content | 850 ppm |
| (iv) Exchange pH | 6 |
| (v) Pore diameter | 85 Å |

(b) Impregnation of the product silica with aqueous solution of hydrofluoric acid The reactor was opened and 90 cm³ of a 45% aqueous HF solution were added. The aqueous solution was circulated through the bed of silica gel. The silica gel was then dried for 24 hours at 200° C.

The characteristics of the product silica were as follows:

| (i) Specific surface | 294 m²/g |
|---|---|
| (ii) Total pore volume | 75 cm³/100 g |
| (iii) Na₂O content | 750 ppm |
| (iv) Exchange pH | 2.2 |
| (v) Pore diameter | 90 Å |
| (vi) Fluorine content | 1.6% |

(c) Preparation of meta-trifluoromethylbenzonitrile from meta-trifluoromethylformanilide Into a one liter, stainless steel tubular reactor filled with the catalyst prepared according to the aforesaid steps (a) and (b), a mixture of 16.1 kg meta-trifluoromethylformanilide and 64.6 kg acetonitrile was continuously introduced, over the course of 150 hours.

The reaction temperature was maintained at 530° C. throughout the catalytic bed.

The following products were recovered upon distillation of the reaction solvent and the water of reaction:
(1) 12 kg meta-trifluoromethylbenzonitrile;
(2) 1.25 kg meta-trifluoromethylaniline;
(3) 0.2 kg Unconverted formanilide; and
(4) 1.2 kg Heavy products.

Nitrile selectivity was 91.6%. The fluoride content in the crude mixture exiting the reactor was 350 ppm.

In this example, as in the examples hereinafter, selectivity is defined as the ratio of product nitrile to the formanilide reacted, excluding the formanilide converted into the corresponding anilide, because the latter may be industrially quantitatively converted with formic acid into the beginning formanilide and recycled.

EXAMPLE 2

2250 g of the silica prepared according to Example 1(a) (1) were introduced into a reactor containing three liters of water. The silica was completely immersed. The mixture was heated until a relative pressure of 1 bar was established in the reactor. This pressure was maintained for 3 hours. The resultant silica was dried for 3 hours at 200° C.

The silica treated as aforesaid had the following characteristics:

| (i) Specific surface | 235 m²/g |
|---|---|
| (ii) Total pore volume | 80 cm³/100 g |
| (iii) Na₂O content | 1000 ppm |
| (iv) Exchange pH | 6 |
| (v) Pore volume | 90 Å |

(b) Impregnation with aqueous solution of hydrofluoric acid 500 g of the silica prepared as above were introduced into a rotating bowl mixer. 550 g of an aqueous solution containing 10 g HF were sprayed onto the rotating grains. The grains were then dried at 200° C. for 24 hours.

The produced silica had the following characteristics:

| (i) Specific surface | 220 m²/g |
|---|---|
| (ii) Total pore volume | 80 cm³/100 g |
| (iii) Na₂O content | 1000 ppm |
| (iv) Exchange pH | 2.8 |
| (v) Pore diameter | 95 Å |
| (vi) F content | 1.7% |

(c) Preparation of meta-trifluoromethylphenylacetonitrile from meta-trifluoromethylbenzylformamide Following the procedure of Example 1(c), a mixture of 17.9 kg meta-trifluoromethylbenzylformamide and 71.6 kg acetonitrile was continuously charged into the reactor, over the course of 150 hours.

The reaction temperature was maintained at 530° C. throughout the catalytic bed.

After distillation of the reaction solvent and the water of reaction, the following products were recovered:
(1) 14.3 kg Meta-trifluoromethylphenylacetonitrile;
(2) 1.1 kg Meta-trifluoromethylbenzylamine;
(3) 0.55 kg Uncoverted benzylformamide; and
(4) 0.33 kg Heavy products.

Nitrile selectivity was 98%.
The fluoride content was 350 ppm.

EXAMPLE 3

(a) Impregnation of the silica prepared according to Example 2(a) with aqueous solution of hydrofluoric acid A portion of the silica obtained according to Example 2(a) was introduced into a rotating bowl mixer. An aqueous solution containing 20 g HF was sprayed onto the rotating grains. The grains were then dried at 200° C. for 24 hours.

The product silica had the following characteristics:

| (i) Specific surface | 210 m²/g |
|---|---|
| (ii) Total pore volume | 80 cm³/100 g |
| (iii) Na₂O content | 1000 ppm |
| (iv) Exchange pH | 2.7 |
| (v) Pore diameter | 100 Å |
| (vi) F content | 1.8% |

(b) Preparation of para-fluorobenzonitrile from para-fluoroformanilide

Following the procedure of Example 1(c), 45 kg para-fluoroformanilide and 180 kg acetonitrile were continuously charged into the reactor over the course of 300 hours, at a catalyst bed temperature of 520° C.

After the distillation of the reaction solvent and the water of reaction, the following products were recovered:

(1) 32.8 kg Para-fluorobenzonitrile;
(2) 4.3 kg Para-fluoroaniline;
(3) 0.5 kg Unconverted formanilide; and
(4) 2 kg Heavy products.

Nitrile selectivity was 95%.
The fluoride content was 60 ppm.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A process for the preparation of an aromatic or aliphatic nitrile having the formula:

$$Ar-A-CN \qquad (I)$$

wherein Ar is a benzene radical and A is a direct chemical bond or a hydrocarbon radical having from 1 to 6 carbon atoms, comprising heating to a temperature ranging from about 450° C. to about 550° C. a formamide or formanilide having the formula:

$$Ar-A-NHCHO \qquad (II)$$

or an amide having the formula:

$$Ar-A-CONH_2 \qquad (III)$$

in the presence of a fluorinated siliceous catalyst, said catalyst having been prepared by (i) impregnating a particulate silica prepared by the precipitation of sodium silicate with sulfuric acid, with a dilute aqueous solution of hydrofluoric acid, said hydrofluoric acid solution having a concentration in HF of less than about 5% by weight, and the ratio by weight of the hydrofluoric acid contained in said aqueous solution thereof to the silica being less than about 5%, followed by (ii) drying the catalyst thus impregnated.

2. The process as defined by claim 1, said impregnation (i) being carried out by soaking the silica particulates in said solution of hydrofluoric acid.

3. The process as defined by claim 1, said impregnation (i) being carried out by spraying an atomized spray of said solution of hydrofluoric acid upon said silica particulates.

4. The process as defined by claim 1, said silica particulates having a specific surface ranging from about 200 to about 350 m³/g, a total pore volume ranging from about 50 to about 100 cm³/g, an average pore diameter ranging from about 70 to 100 Å, an exchange pH less than about 7 and a sodium content, expressed as Na₂O, of less than about 1% by weight relative to the silica.

5. The process as defined by claim 4, said hydrofluoric acid solution having a concentration in HF of from about 0.04% to about 4% by weight.

6. The process as defined by claim 4, said impregnation (i) being carried out at ambient temperature, under atmospheric pressure.

7. The process as defined by claim 4, said drying (ii) being carried out at a temperature ranging from about 150° C. to 600° C., for from about 1 to about 24 hours.

8. The process as defined by claim 4, said silica particulates, after the drying (ii) thereof, comprising from about 0.3% to about 3% by weight of bonded fluorine.

9. The process as defined by claim 1, wherein Ar is phenyl or phenyl substituted with at least one of the substituents, alkyl or alkoxy having from 1 to 6 carbon atoms, phenyl, phenoxy, F, CF₃, OCF₃, SCF₃, OH, Cl, Br and CN.

10. The process as defined by claim 9, wherein Ar is phenyl substituted with at least one of the substituents, F, CF₃, OCF₃ and SCF₃.

11. The process as defined by claim 1, the product nitrile having been prepared from a reactant having the formula (II).

12. The process as defined by claim 1, the product nitrile having been prepared from a reactant having the formula (III).

13. The process as defined by claim 1, with meta-trifluoromethylbenzonitrile being prepared from meta-trifluoromethylformanilide.

14. The process as defined by claim 1, with meta-trifluoromethylphenylacetonitrile being prepared from meta-trifluoromethylbenzylformamide.

15. The process as defined by claim 1, the reaction being carried out in an inert gaseous diluent.

16. The process as defined by claim 15, said inert gaseous diluent comprising nitrogen, carbon dioxide, acetonitrile, or admixture thereof.

17. The process as defined by claim 15, said inert gaseous diluent being acetonitrile, employed in an amount such that the molar percentage of the reactant (II) or (III) in the acetonitrile ranges from about 2 to about 20.

18. The process as defined by claim 4, for the preparation of one of the nitriles: benzonitrile, 3-trifluoromethylbenzonitrile, 4-trifluoromethylbenzonitrile, 4-methoxybenzonitrile, 4-hydroxybenzonitrile, 2-fluorobenzonitrile, 3-fluorobenzonitrile, 4-fluorobenzonitrile, 2-chlorobenzonitrile, 3-chlorobenzonitrile, 4-chlorobenzonitrile, 2-chloro-5-trifluoromethylbenzonitrile, 3-trifluoromethyl-4-chlorobenzonitrile, 3-phenoxybenzonitrile, 3,5-bis-trifluoromethylbenzonitrile, 2,6-dichlorobenzonitrile, 2,6-difluorobenzonitrile, 2,4-difluorobenzonitrile, 3-trifluoromethylthiobenzonitrile, 4-trifluoromethoxybenzonitrile, phenylacetonitrile, 3-trifluoromethylphenylacetonitrile, 4-trifluoromethylphenylacetonitrile, 4-fluorophenylacetonitrile, 4-chlorophenylacetonitrile, 2-fluorophenylacetonitrile, 2-chlorophenylacetonitrile, 2-trifluoromethoxyphenylacetonitrile, 4-trifluoromethoxyphenylacetonitrile, 2-trifluoromethylthiophenylacetonitrile, 4-trifluoromethylthiophenylacetonitrile, 2-fluoro-5-methylphenylacetonitrile, 3-fluoro-6-methylphenylacetonitrile, 2-chloro-5-trifluoromethoxyphenylacetonitrile, 2-trifluoromethoxy-5-chlorophenylacetonitrile, 2,5-difluorophenylacetonitrile, 2,4-difluorophenylacetonitrile.

* * * * *

UNITED STATES PATENT AND TRADEMARK OFFICE
CERTIFICATE OF CORRECTION

PATENT NO. : 4,438,042
DATED : March 20, 1984
INVENTOR(S) : Jacques et al

It is certified that error appears in the above-identified patent and that said Letters Patent is hereby corrected as shown below:

Title page, column 1, at [30] Foreign Application Priority Data: "May 15, 1982 [FR]" should read --May 15, 1981 [FR]--.

Signed and Sealed this

Sixteenth Day of July 1985

[SEAL]

Attest:

DONALD J. QUIGG

*Attesting Officer*  *Acting Commissioner of Patents and Trademarks*